United States Patent [19]

Dixon

[11] Patent Number: Plant 7,625

[45] Date of Patent: Aug. 20, 1991

[54] RASPBERRY PLANT NAMED 'GRATON GOLD'

[76] Inventor: David Dixon, 12225 Graton Rd., Sebastopol, Calif. 95472

[21] Appl. No.: 444,452

[22] Filed: Nov. 30, 1989

[51] Int. Cl.[5] ..... A01H 5/00

[52] U.S. Cl. ..... Plt./46

[58] Field of Search ..... Plt./46

[56] References Cited

U.S. PATENT DOCUMENTS

P.P. 113 11/1934 Curtis ..... Plt. 46

P.P. 3,717 5/1975 Hagerstrom ..... Plt. 46

OTHER PUBLICATIONS

Jennings, D. L., "Chapter 14 Flowers and Fruit" *Raspberries and Blackberries: Their Breeding; Diseases and Growth* 1988 Academic Press, San Diego, pp. 171–173.

*Primary Examiner*—James R. Feyrer

[57] ABSTRACT

A new variety of yellow raspberry having a deeper yellow color than 'Fall Gold'. The variety is further characterized by its habit of flowering and fruiting about the same time as 'Heritage' and a better flavor than 'Fall Gold'. Also, the new variety has a greater yield than 'Fall Gold' in that it produces two to three times the number of berries per panicle. The berry of the new variety has a greater firmness than that of 'Fall Gold'.

2 Drawing Sheets

BACKGROUND AND ASEXUAL REPRODUCTION OF THE VARIETY

The present invention relates to a new and distinct variety of yellow raspberry named 'Graton Gold'.

'Graton Gold' was discovered on my farm in Sebastopol, Sonoma County, Calif., in 1987. From a field of raspberries of the 'Heritage' variety which had been planted in March 1985, I noticed occasional yellow berries appearing in the production from this field. The 'Heritage' plants were obtained from the certified nursery in Oregon, which does not propagate yellow raspberries. The cane bearing the yellow fruit which I observed was marked to identify it. In the following season four canes grew in the same place which had produced this yellow fruit. In the winter of 1988/89 the plant was dug up and was asexually reproduced by root division. Five new plants were propagated and each of the five plants were true to the mother plant and produced yellow fruit on the primocanes in the summer of 1989.

Figure 1:
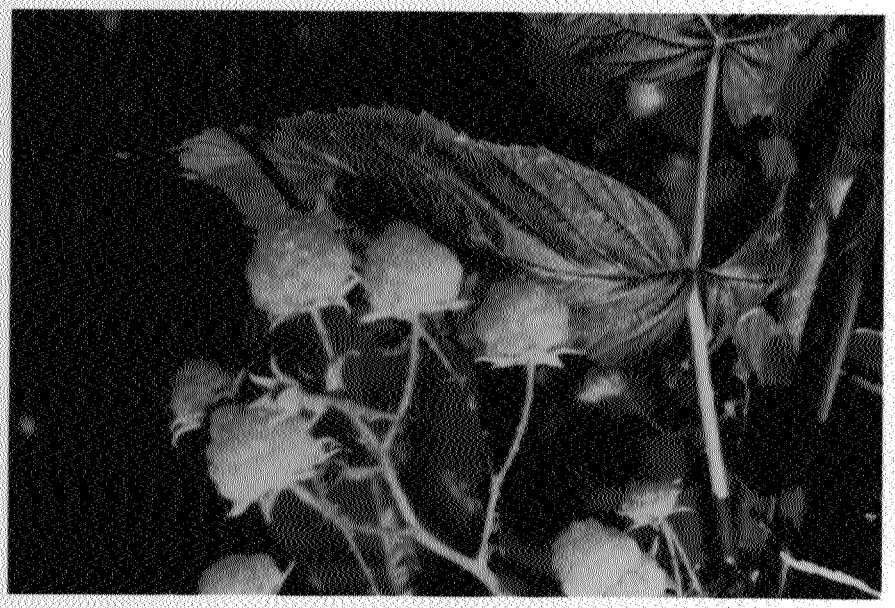
FIG. 1 shows cane, leaves and berry clusters typical of the plant of the new variety with the unique yellow color of ripe fruit.
Figure 2:
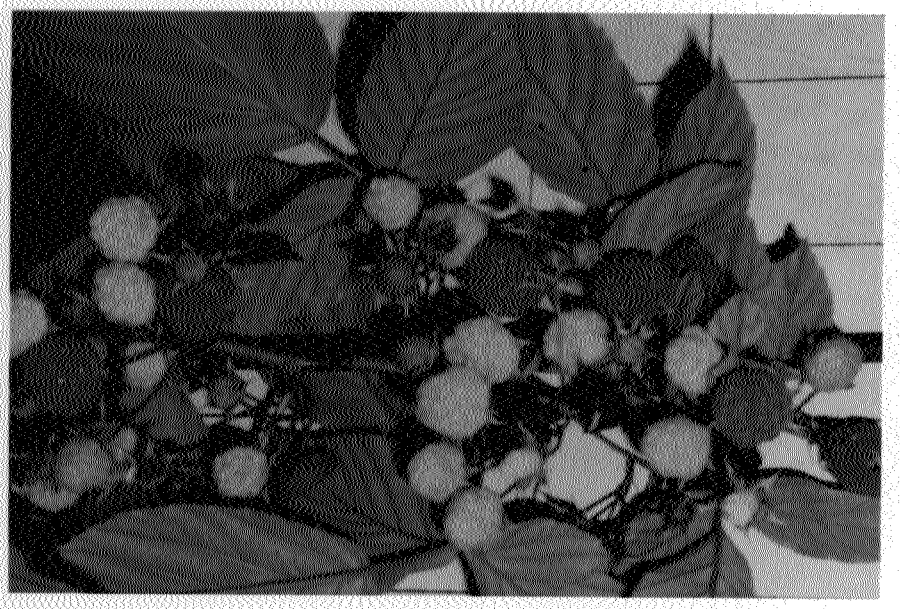
FIG. 2 shows the cane, leaves and berry clusters typical of the plant of the new variety and in which the berries appear as orange red when overripe.
Figure 3:
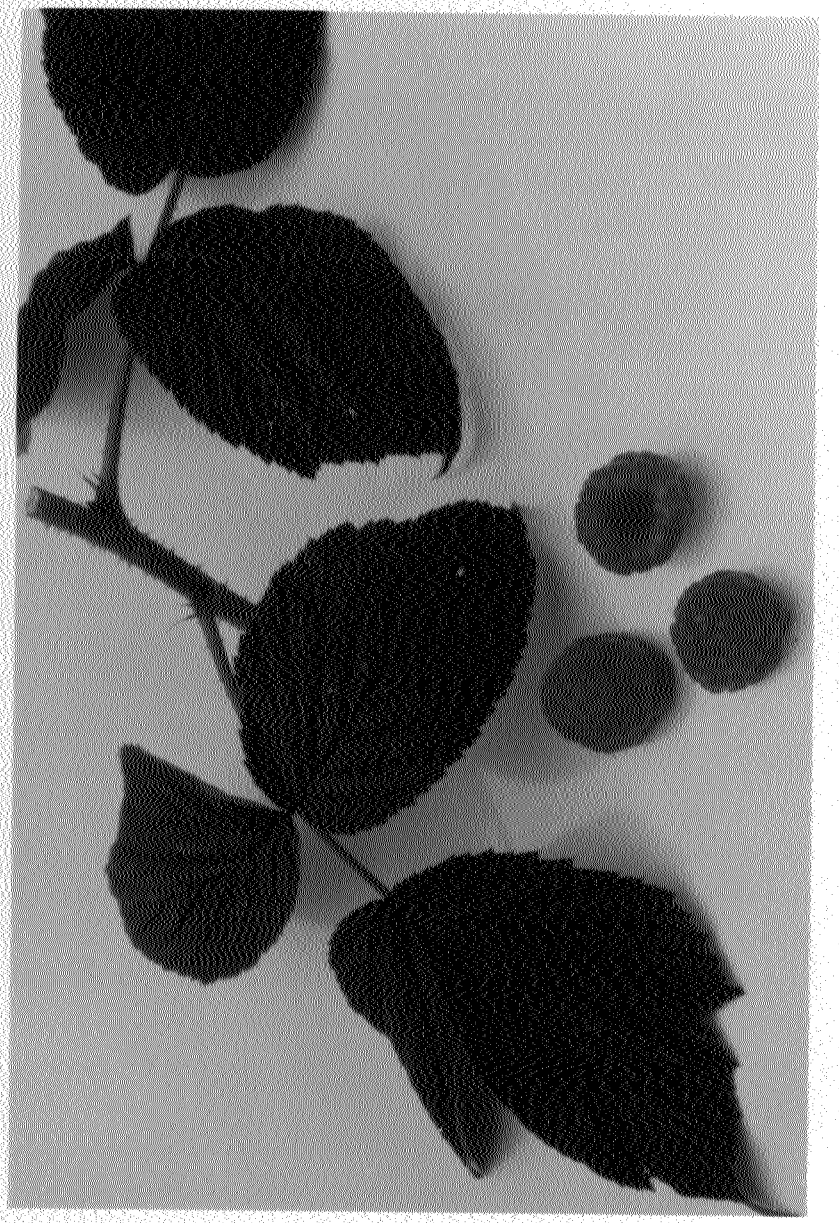
FIG. 3 depicts a short segment of a typical cane, leaves, leaf shape, leaf margins, leaf surface texture, axillary buds and typical fruit of mature to over mature stage of ripeness. Color definitions presented within the specification have been taked from the Royal Horticultural Society (R.H.S.) Colour Chart.

The new variety has displayed the following novel characteristics:

1. Unique color which is a deeper yellow than other yellow varieties such as 'Fall Gold';
2. Improved flavor over 'Fall Gold';

3. Greatly increased yield over 'Fall Gold' based upon the number of berries per panicle, i.e., two to three times that of 'Fall Gold' and
4. Greater firmness than that of 'Fall Gold'.

'Graton Gold' will flower and fruit at the same time as 'Heritage' and produces a heavier primocane crop. The spring crop starts about May 20 on the floricanes, and the main primocane fall crop starts about August 28, to continue until about mid October, in Graton Calif. In general, the plant is similar to its parent, 'Heritage', except that it has a lack of red pigmentation in the fruit, stem, spines and leaves, which is possibly caused by gene T being replaced by its recessive allele t.

BOTANICAL DESCRIPTION

The following is a detailed description of the plant and its parts with colors specified according to the Royal Horticultural Society Colour Chart.

Plant: Everbearer, bearing on primocanes and floricanes.

Canes: Upright to semi-upright reaching a height of 5 to 7 feet or approximately 2 meters, and covered with small (2 mm) prickles. Primocanes are nonbranching upright until heavily laden with fruit when they tend to lean over and require support. The stem is bright green, 143C as compared to 'Fall Gold' which is a lighter green, 145C and has a somewhat glaucus appearance. Stem and prickles turn light brown with age. The floricanes are light brown and branching. 'Heritage' shows shades of red on the canes, prickles, and older leaves.

Foliage: Typically five foliate, low down on the canes, tri-foliate towards the top and cordate, occasionally developing single lobes or one lobe on each side. Lobe formation ranges from mere points to independent leaflets. Leaves are green, 136B for lower leaves to 141A for top leaves and have no red.

Fruit: Born on panicles with the terminal cluster typically bearing 3 to 4 fruits and lower clusters bearing considerably more, typically 10–15 berries with some nodes producing double panicles with up to 25 fruits per node. The berries are medium size, average weight about 2.2 grams comprised of 60–80 druplets. Druplets have a prominent median depression. The fruit is generally round in shape. The receptacle is cylindrical at its base where sepals and dry stamens remain attached. The receptacle then tapers to a rounded point. Fruit color is orange, 25C, when ripe enough to pick, deepening to orange red, 31A when overripe and on the point of falling off the plant when touched.

Sweetness and Flavor: The fruit typically has total dissolved solids of 10.3° Brix as compared to 13° Brix for 'Fall Gold'. The titratable acid of 'Graton Gold' is about the same as 'Fall Gold'. The flavor is typical of red raspberries and would be rated as good to excellent.

Yield: Yield of 'Graton Gold' is about two to three times of that of 'Fall Gold'.

I claim:

1. I claim the new and distinct variety of Yellow Raspberry plant having the characteristics described and illustrated herein.

* * * * *